United States Patent
Lee et al.

(10) Patent No.: US 10,441,339 B2
(45) Date of Patent: Oct. 15, 2019

(54) SPINAL TISSUE ABLATION APPARATUS, SYSTEM, AND METHOD

(71) Applicant: Medtronic Holding Company Sàrl, Tolochenaz (CH)

(72) Inventors: Stephen W. Lee, San Jose, CA (US); Michael A. Smith, San Jose, CA (US); Dawud F. Dueiri, Santa Clara, CA (US)

(73) Assignee: Medtronic Holding Company Sàrl, Tolochenaz (CH)

( * ) Notice: Subject to any disclaimer, the term of this patent is extended or adjusted under 35 U.S.C. 154(b) by 875 days.

(21) Appl. No.: 14/943,264

(22) Filed: Nov. 17, 2015

(65) Prior Publication Data
US 2017/0135742 A1    May 18, 2017

(51) Int. Cl.
*A61B 18/00* (2006.01)
*A61B 18/08* (2006.01)
*A61B 18/10* (2006.01)

(52) U.S. Cl.
CPC ............ *A61B 18/082* (2013.01); *A61B 18/10* (2013.01); *A61B 2018/00023* (2013.01); *A61B 2018/00041* (2013.01); *A61B 2018/0072* (2013.01); *A61B 2018/00339* (2013.01); *A61B 2018/00577* (2013.01); *A61B 2018/00642* (2013.01); *A61B 2018/00744* (2013.01); *A61B 2018/00797* (2013.01); *A61B 2018/00821* (2013.01); *A61B 2018/00875* (2013.01)

(58) Field of Classification Search
CPC ........... A61B 2018/00821; A61B 2018/00994; A61B 2018/00041
See application file for complete search history.

(56) References Cited

U.S. PATENT DOCUMENTS

| 4,946,460 A | * | 8/1990 | Merry | A61B 18/02 606/21 |
| 5,100,388 A |  | 3/1992 | Behl et al. | |
| 5,261,399 A | * | 11/1993 | Klatz | A61F 7/10 607/104 |

(Continued)

FOREIGN PATENT DOCUMENTS

JP    3756522 B2    3/2006

OTHER PUBLICATIONS

International Search Report and Written Opinion for PCT/US2016/061557 the counterpart application dated Feb. 16, 2017, 9 pages.

(Continued)

*Primary Examiner* — Ronald Hupczey, Jr.

(57) ABSTRACT

Flexible apparatus for ablating unhealthy spinal tissue. A housing includes a distal end and a proximal end. Multiple thermocouples mounted on the housing measure spinal tissue temperatures at locations between the proximal end and the distal end. A sensor measures spinal tissue impedance. The measured spinal tissue impedance corresponds to various physical state data of the spinal tissue. The spinal tissue impedance and the spinal tissue temperatures are displayed to the surgeon, enabling the surgeon to determine with certainty the location of the unhealthy spinal tissue, and to exercise control over the ablation apparatus. Nerve stimulation by IMP/STM switch system to detect nerve responses before and after treatment.

31 Claims, 5 Drawing Sheets

(56) References Cited

U.S. PATENT DOCUMENTS

| | | | |
|---|---|---|---|
| 5,462,552 A | 10/1995 | Kiester | |
| 5,843,086 A | 12/1998 | Huyser et al. | |
| 6,066,139 A * | 5/2000 | Ryan | A61B 18/1206 606/135 |
| 6,190,378 B1 * | 2/2001 | Jarvinen | A61B 18/02 606/20 |
| 6,293,943 B1 | 9/2001 | Panescu et al. | |
| 6,468,268 B1 * | 10/2002 | Abboud | A61B 18/02 606/20 |
| 6,562,033 B2 | 5/2003 | Shah et al. | |
| 6,845,264 B1 | 1/2005 | Skladnev et al. | |
| 6,858,025 B2 * | 2/2005 | Maurice | A61B 18/02 128/898 |
| 6,881,214 B2 | 4/2005 | Cosman et al. | |
| 7,108,696 B2 | 9/2006 | Daniel et al. | |
| 7,160,296 B2 | 1/2007 | Pearson et al. | |
| 7,824,398 B2 | 11/2010 | Woloszko et al. | |
| 7,824,404 B2 | 11/2010 | Godara et al. | |
| 8,473,067 B2 | 6/2013 | Hastings et al. | |
| 8,512,335 B2 | 8/2013 | Cheng et al. | |
| 8,591,507 B2 | 11/2013 | Kramer et al. | |
| 8,667,674 B2 | 3/2014 | Buysse | |
| 8,709,087 B2 | 4/2014 | Cragg | |
| 8,936,594 B2 | 1/2015 | Wolf et al. | |
| 8,936,631 B2 | 1/2015 | Nguyen et al. | |
| 2001/0023348 A1 | 9/2001 | Ashley | |
| 2003/0148247 A1 | 8/2003 | Sicurelli, Jr. et al. | |
| 2003/0171744 A1 | 9/2003 | Leung | |
| 2004/0127963 A1 | 7/2004 | Uchida | |
| 2005/0177210 A1 | 8/2005 | Leung | |
| 2008/0021465 A1 | 1/2008 | Shadduck et al. | |
| 2008/0051777 A1 | 2/2008 | Haemmerich | |
| 2009/0312806 A1 | 12/2009 | Sherman et al. | |
| 2010/0211058 A1 | 8/2010 | Winterbottom et al. | |
| 2011/0022041 A1 | 1/2011 | Ingle et al. | |
| 2011/0166518 A1 | 7/2011 | Nguyen | |
| 2012/0016174 A1 | 1/2012 | De Taboada et al. | |
| 2013/0226271 A1 | 8/2013 | Ferree | |
| 2013/0253518 A1 | 9/2013 | Mitchell et al. | |
| 2013/0324996 A1 | 12/2013 | Pellegrino et al. | |

OTHER PUBLICATIONS

Supplementary European Search Report dated Jun. 18, 2019 of corresponding European Application No. 16866893.7.

* cited by examiner

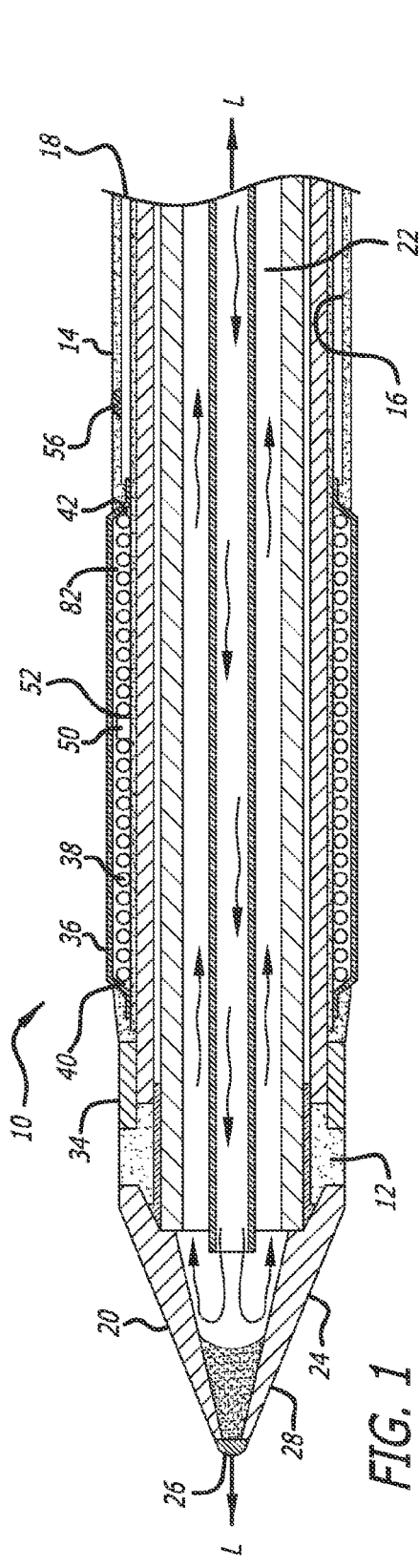
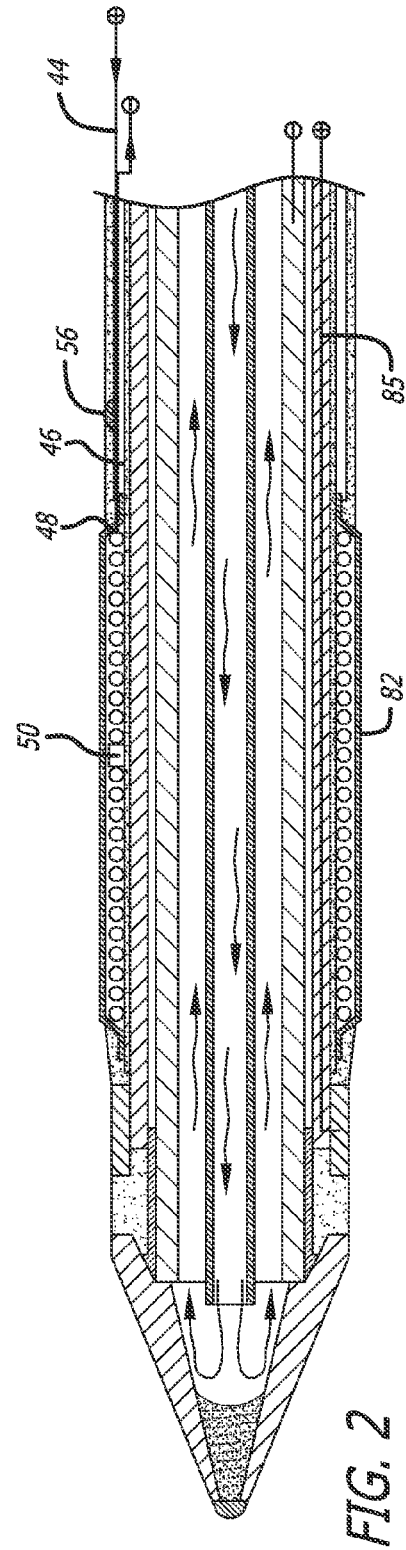
FIG. 1
FIG. 2

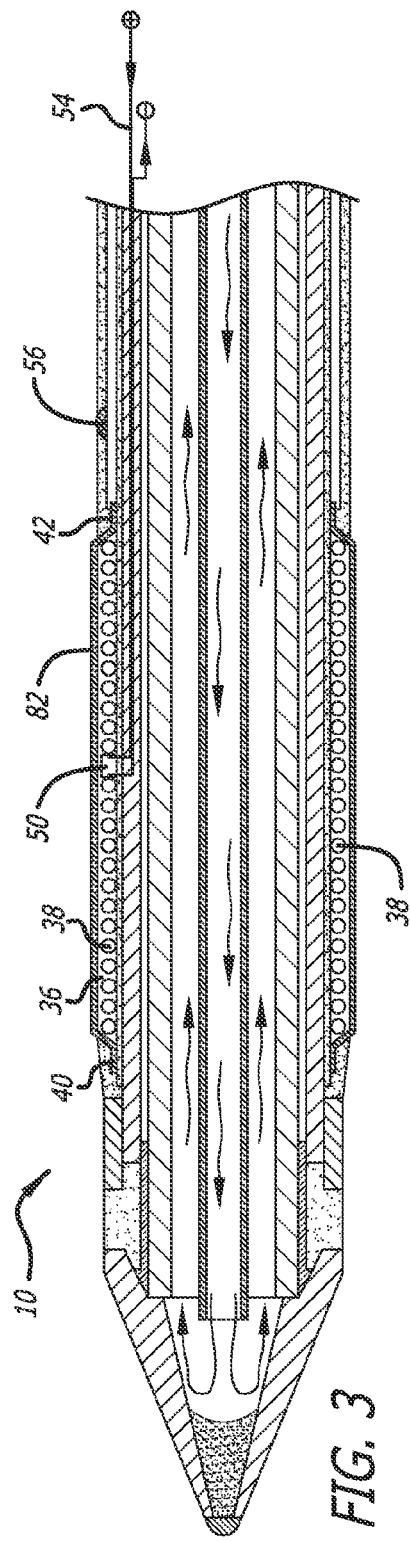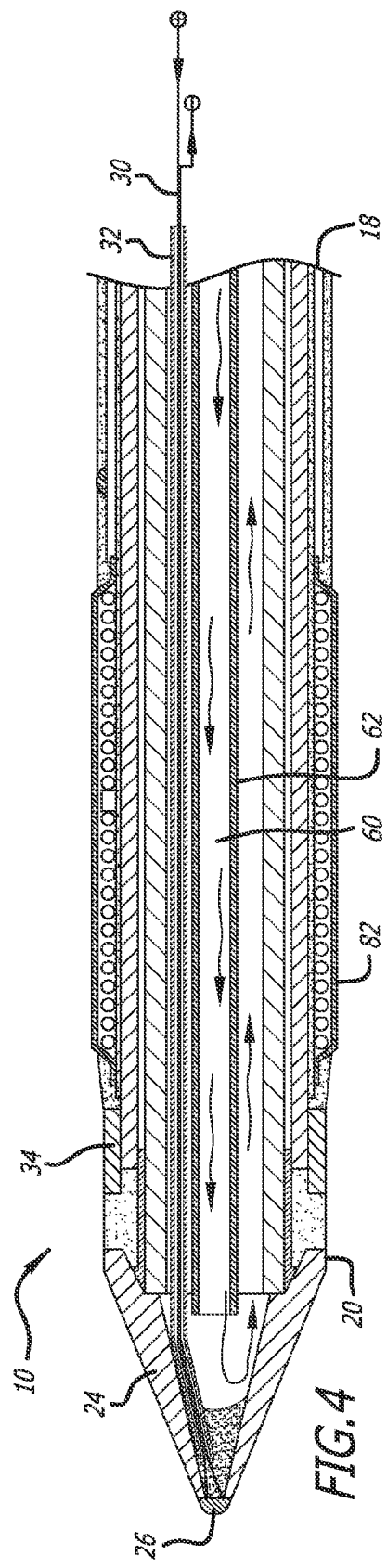

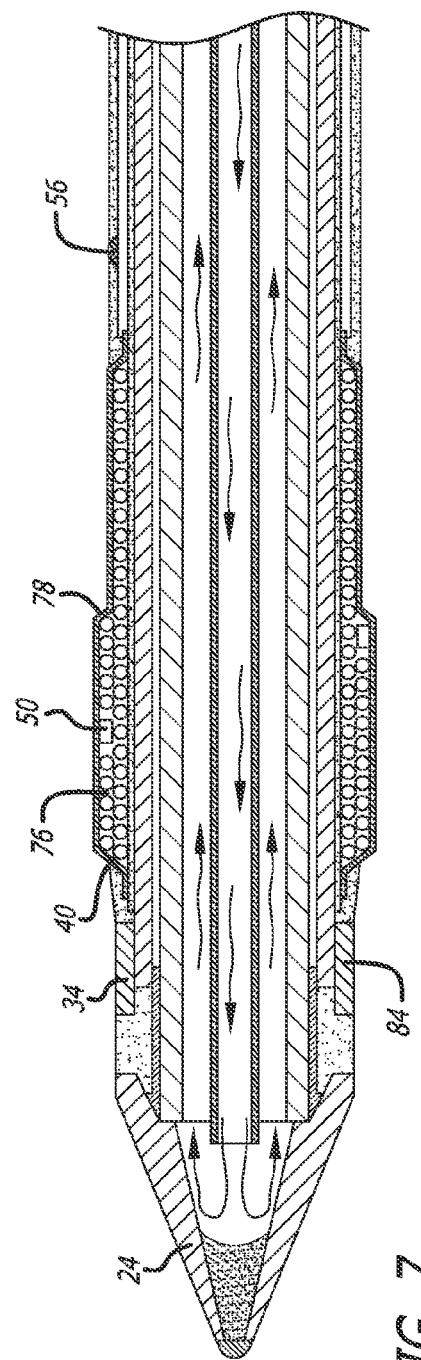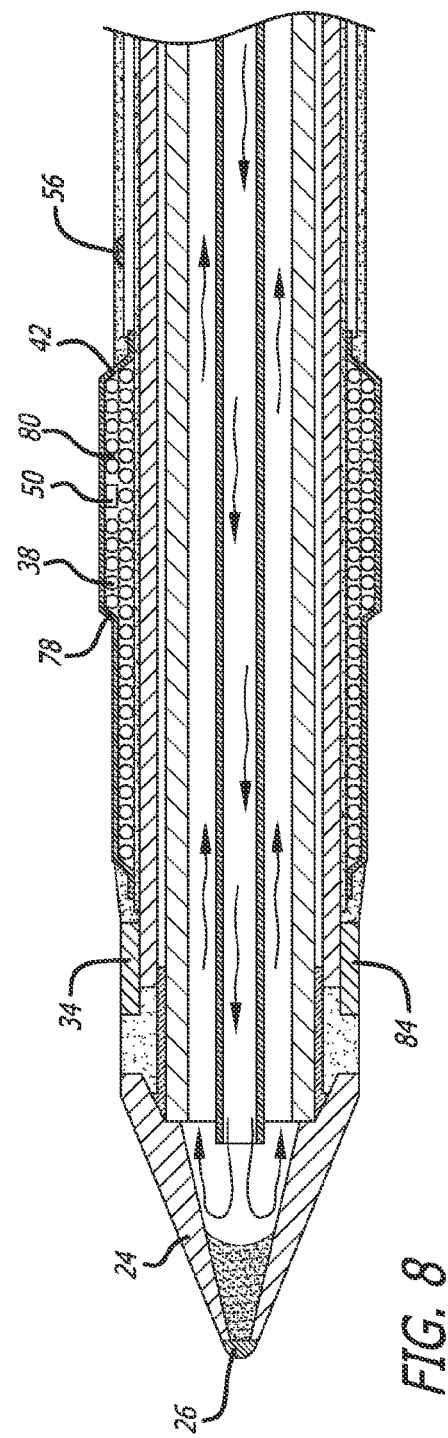

SPINAL TISSUE ABLATION APPARATUS, SYSTEM, AND METHOD

BACKGROUND OF THE INVENTION

Field of the Invention

The present invention relates to an apparatus, a system, and a method for ablating unhealthy spinal tissue, particularly unhealthy and spinal nerve tissue in a disc space between two adjacent vertebral bodies.

Description of the Related Art

Devices and methods for ablating unhealthy spinal tissue in a patient, particularly unhealthy spinal nerve tissue in a disc space between two adjacent vertebral bodies are known. Existing electrode ablation devices, whether monopolar or bipolar devices, and their associated systems, however, lack precise control of power level and temperature; require overly-long treatment times; often inadvertently ablate healthy spinal tissue adjacent to the unhealthy spinal tissue; are insufficiently flexible to reach all locations of unhealthy spinal tissue in the disc space; and provide the surgeon with inadequate control over the ablation procedure.

SUMMARY OF THE INVENTION

It is an object of the present invention to provide an apparatus for ablating unhealthy and necrotic spinal tissue in a patient, which obviates one or more of the shortcomings of the related art.

It is another object of the present invention to provide an apparatus for ablating unhealthy and necrotic spinal tissue at a surgical site in a patient, particularly in a disc space between two vertebral bodies.

The apparatus includes an elongated housing. The housing includes an outer surface, an inner surface, a proximal end, and a distal end. The proximal end and the distal end define a mid-longitudinal axis. The inner surface defines an interior space.

An anode is defined on the outer surface of the housing at the distal end. A first thermocouple is defined on an outer surface of the anode. The first thermocouple is configured to measure temperature of spinal tissue proximate the anode.

A cathode is defined on the outer surface of the housing, intermediate the proximal end and the distal end.

A first layer of resistive heating elements substantially encircle, relative to the mid-longitudinal axis, the outer surface of the housing, extending in a proximal direction from a first position proximate the cathode to a second position intermediate the first position and the proximal end of the housing.

A recirculating water cooling system is provided in the interior space of the housing.

A second thermocouple is disposed on the outer surface of the housing at an integrated position. The integrated position is integrated with the resistive heating elements. The second thermocouple is configured to measure temperature of spinal tissue proximate the integrated position.

A third thermocouple is disposed in the housing proximate the proximal end of the housing. The third thermocouple is configured to measure temperature of spinal tissue proximate the proximal end of the housing, including spinal tissue proximate the spinal cord.

At least one sensor is provided on the housing. The at least one sensor is configured to measure impedance of the spinal tissue proximate the ablation apparatus at the surgical site.

The housing of the ablation apparatus is configured to be flexible.

It is another object of the present invention to provide a system for ablating unhealthy spinal tissue. In accordance with the invention, the system includes the above-described spinal tissue ablation apparatus.

In accordance with one preferred embodiment of the invention, the system further includes a power generator. The power generator includes, among other things, a detector, a touch screen display, a control module, a human interface panel, and impedance detection/nerve stimulation ("IMP/STM") switch. In some embodiments, the power generator also may include an RF transmitter/receiver. The detector is configured to receive the spinal tissue temperatures measured by the first, second, and third thermocouples, and to receive the spinal tissue impedance measured by the at least one sensor. The detector is further configured to transmit the spinal tissue temperatures and the spinal tissue impedance to the touch screen display, which is visible to the surgeon performing the spinal tissue ablation process. The human interface panel allows the surgeon to control the ablation apparatus, based on his professional judgment in view of the feedback on the touch screen display.

For example, the surgeon may increase ablation heat by increasing electric current flow to the resistive heating elements, or by reducing coolant flow through the cooling system in the interior space of the housing.

Likewise, the surgeon may decrease ablation heat by reducing electric current flow to the resistive heating elements, or by increasing coolant flow through the cooling system in the interior space of the housing.

Alternately, the surgeon may adjust the position of the ablation apparatus within the surgical site, utilizing the flexibility of the housing to perform this adjustment, or withdraw the ablation apparatus from the surgical site.

It is a further object of one preferred embodiment of the present invention to provide a method for ablating unhealthy spinal tissue, particularly unhealthy and necrotic spinal nerve tissue, in a disc space between an upper vertebral body and a lower vertebral body.

The method includes utilizing the spinal tissue ablation system described above, including the spinal tissue ablation apparatus, and the power generator.

The method further includes preparing a surgical site in a patient, in the spinal region of the patient, particularly in a disc space between two vertebral bodies. The surgical site includes unhealthy spinal tissue, including unhealthy spinal nerve tissue. The surgical site may also include healthy spinal tissue.

The method further includes inserting the spinal tissue ablation apparatus to a desired location in the surgical site, flexing the housing as necessary to reach the desired location in the surgical site. Heat is applied to the surgical site by closing a switch in the handle of the ablation apparatus to direct electric current to at least the first layer of resistive heating elements of the ablation apparatus. The first, second, and third thermocouples measure temperature of the spinal tissue proximate each respective thermocouple. The first thermocouple, second thermocouple, and third thermocouple transmit the respective measured spinal tissue temperatures to the detector. The IMP/STM switch is switched to the STM mode, sending a low power pulse to the at least one sensor, to stimulate ionic flow between the anode and the cathode. The at least one sensor measures impedance of the spinal tissue at the surgical site proximate the ablation apparatus. The at least one sensor transmits the measured spinal tissue impedance to the detector. The impedance data corresponds to a physical state of the tissue, e.g., whether the tissue is healthy spinal bone tissue, healthy spinal nerve tissue, or tumorous tissue. The at least one sensor transmits the measured spinal tissue impedance to the detector. The spinal tissue impedance and the spinal tissue temperatures are displayed on the touch screen display.

In one embodiment of the invention, the surgeon may elect, based on the spinal tissue impedance and the spinal tissue temperatures displayed on the touch screen display, to exert further control of the ablation procedure, using one or more of the steps described above.

These and other objects of the present invention will be apparent from review of the following specification and the accompanying drawings.

BRIEF DESCRIPTION OF THE DRAWINGS

FIG. 1 is a side cross-sectional view of one embodiment of a spinal tissue ablation apparatus in accordance with the invention;

FIG. 2 is a side cross-sectional view of the spinal tissue ablation apparatus of FIG. 1, depicting an electrical connection for a first layer of resistive heating elements encircling a portion of the outer surface of the housing, and an electric connection for an impedance-measuring sensor;

FIG. 3 is a side cross-sectional view of the spinal tissue ablation apparatus of FIG. 1, depicting an electrical connection for a thermocouple mounted in an integrated position with the first layer of resistive heating elements;

FIG. 4 is a side cross-sectional view of the spinal tissue ablation apparatus of FIG. 1, depicting an electrical connection for a thermocouple mounted in an anode at a distal end of the ablation apparatus;

FIG. 7 is a side cross-sectional view of another embodiment of a spinal tissue ablation apparatus in accordance with the invention, having a partial distal second layer of resistive heating elements overlying the distal end of the first layer of resistive heating elements;

FIG. 8 is a side cross-sectional view of another embodiment of a spinal tissue ablation apparatus in accordance with the invention, having a partial proximal second layer of resistive heating elements overlying the proximal end of the first layer of resistive heating elements.

DETAILED DESCRIPTION OF THE PREFERRED EMBODIMENTS

Figure 5:
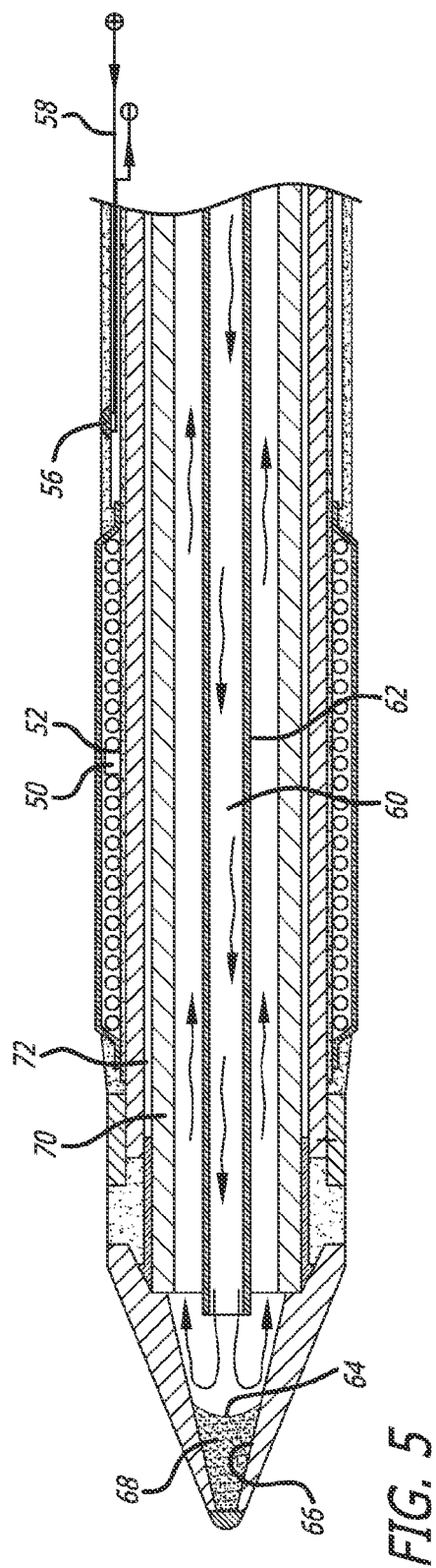
FIG. 5 is a side cross-sectional view of the spinal tissue ablation apparatus of FIG. 1, depicting an electrical connection for a thermocouple mounted on the housing proximate the proximal end of the housing.

In accordance with one preferred embodiment of the present invention, and as broadly depicted in FIG. 1, a spinal tissue ablation apparatus 10 is provided for ablating unhealthy spinal tissue.

In accordance with the invention, the spinal tissue ablation apparatus 10 includes an elongated housing 12. Housing 12 includes an outer surface 14, an inner surface 16, a proximal end 18, and a distal end 20. The inner surface 16 defines an interior space 22. A mid-longitudinal axis L-L is defined between the proximal end 18 and the distal end 20.

As used herein, the term "in the proximal direction" refers to movement toward the proximal end 18, whereas the term "in the distal direction" means movement toward the distal end 20. As depicted in FIG. 1, the housing 12 has a cylindrical configuration, but the invention is not limited to a housing having this configuration.

In accordance with the invention, an anode 24 is defined on the outer surface 14 at the distal end 20. As depicted in FIG. 1, anode 24 has a conical configuration, but the invention is not limited to an anode having this configuration.

Figure 9:
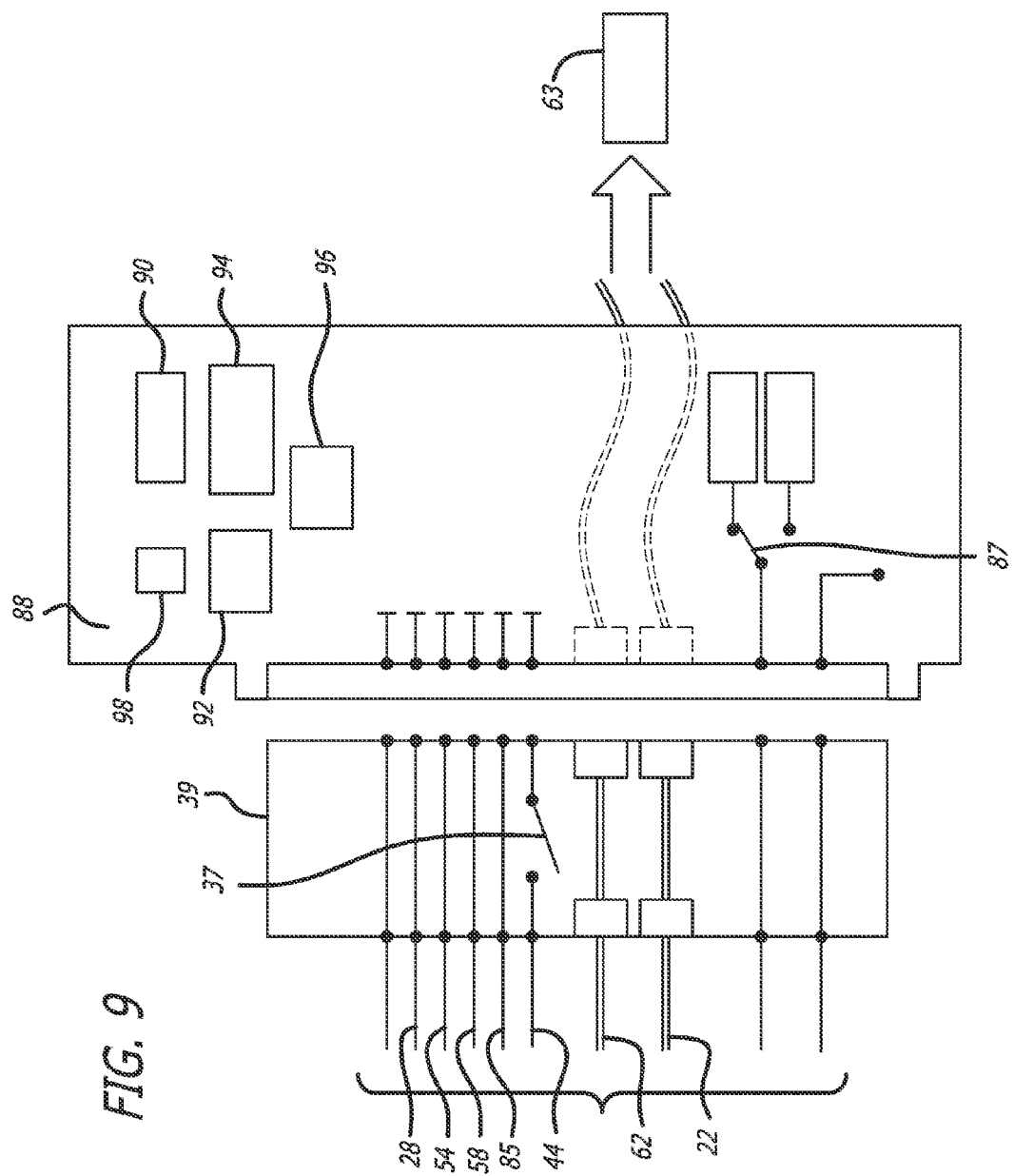
FIG. 9 is a schematic view of a power generator and a handle associated with one embodiment of a spinal tissue ablation system in accordance with the invention.

In accordance with the invention, a first thermocouple 26 is disposed on an outer surface 28 of the anode 24. First thermocouple 26 is configured to measure temperature of spinal tissue adjacent the anode 24. In accordance with the invention, and as depicted in FIGS. 4 and 9, electric power is supplied to the first thermocouple 26 via conductive wires 30, which are enclosed within a waterproof plastic tube 32 as they are routed through the interior space 22 between the proximal end 18 and the distal end 20 of the ablation apparatus 10. In accordance with one preferred embodiment of the invention, each thermocouple is a K-type thermocouple, rated for ambient temperatures of up to approximately 200° C., with an accuracy of ±1° C.

In accordance with the invention, a cathode 34 is defined on the outer surface 14 of the housing 12 proximate, and spaced in the proximal direction away from, the anode 24.

In accordance with the invention, and as depicted in FIG. 1, a first layer 36 of resistive heating elements 38 encircles, with respect to the mid-longitudinal axis, a portion of the outer surface 14 of the housing 12. The first layer 36 of the resistive heating elements 38 extends in the proximal direction from a first position 40 proximate the cathode 34, to a second position 42 intermediate the first position 40 and the proximal end 18. As depicted in FIGS. 1-8, the resistive heating elements 38 include bipolar conductive coils. In accordance with the invention, and as depicted in FIGS. 2 and 9, electric current is supplied to the first layer 36 of resistive heating elements 38 via conductive wires 44, which travel through a space 46 below the inner surface 16. The conductive wires 44 connect to the first layer 36 of resistive heating elements 38 at a terminal 48. As depicted in FIG. 9, the conductive wires 44 are electrically connected to an on/off switch 37, located in a handle 39, at the proximal end 18. When the on/off switch 37 is switched to the on position, electric current is supplied, via the conductive wires 44 to the first layer 36 of resistive heating elements 38.

In accordance with the invention, resistive heating power is up to 20-30 watts, with a voltage control of 0-3 volts, and a current control of 0-10 mA. The resistive heating power is further preferably applied at frequencies of 1.5 Hz, through 200 Hz, for durations of 0.1 msec. through 3 msec.

In accordance with the invention, a second thermocouple 50 is disposed on the outer surface 14 of the housing 12. The second thermocouple 50 is disposed in an integrated position 52. The integrated position 52 is integrated with the resistive heating elements 38. Second thermocouple 50 is configured to measure temperature of spinal tissue adjacent the integrated position 52. In accordance with the invention, and as depicted in FIGS. 3 and 9, electric power to the second thermocouple 50 is provided via conductive wires 54, which are connected to the handle 39 at the proximal end 18.

In accordance with the invention, a third thermocouple 56 is provided on the housing 12, proximate the proximal end 18. The third thermocouple 56 is configured to measure temperature of spinal tissue proximate the proximal end 18. Although the invention is not limited to being used to ablate unhealthy and necrotic spinal tissue in a disc space between two adjacent vertebral bodies, one of ordinary skill in the art will recognize that when the apparatus 10 is inserted into a disc space between two adjacent vertebral bodies, the third thermocouple 56 will be located proximate the patient's spinal cord, in order to measure spinal tissue temperature proximate the spinal cord. In accordance with the invention, and as depicted in FIG. 5, electrical power to the third thermocouple 56 is provided via conductive wires 58, which travel through the space 46.

Figure 6:
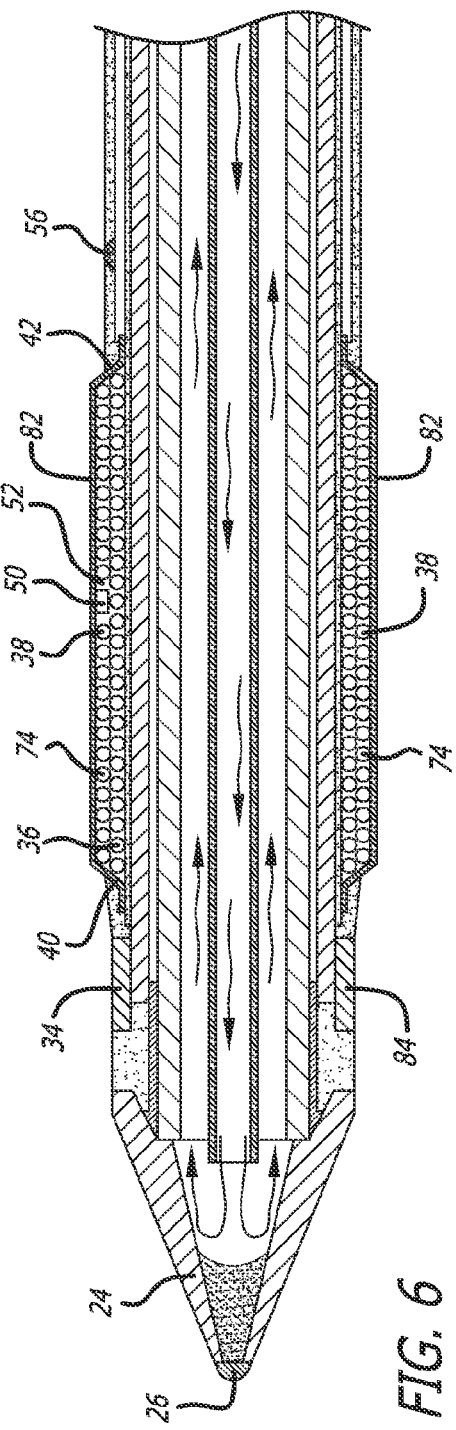
FIG. 6 is a side cross-sectional view of another embodiment of a spinal tissue ablation apparatus in accordance with the invention, having a second layer of resistive heating elements overlying the first layer of resistive heating elements.

In accordance with the invention, a cooling system 60 is provided within the interior space 22 of the housing 12. As depicted in FIGS. 5, 6, and 9, cooling system 60 includes a recirculating water system, including a water pipe 62. The water pipe 62 directs cooling water in the distal direction, within the interior space 22, from the proximal end 18 to the distal end 20. Proximate the distal end 20, the cooling water exits the water pipe 62, and strikes an arcuate wall 64 defined in the distal end 20. Arcuate wall 64 redirects the cooling water flow back in the proximal direction through the interior space 22. The cooling system 60 further includes a pump 63, to which the cooling water pipe 62 and the interior space 22 connect, to recirculate the cooling water. In accordance with the invention, the preferred cooling water recirculation flowrate is approximately 50 ml/minute.

In accordance with one embodiment of the invention, the wall 64 cooperates with an inner surface 66 of the anode 24 to define a reservoir 68. The reservoir 68 is preferably filled with a high temperature epoxy.

In accordance with one embodiment of the invention, at least one insulating layer 70 is defined between the inner surface 16 of the housing 12 and the interior 22. The at least one insulating layer 70 preferably is made of polyethylene terephthalate (PET), but the invention is not limited to this material.

In accordance with one embodiment of the invention, an air-filled gap 72 is provided between the at least one insulating layer 70 and the inner surface 16. The air-filed gap 72 provides the housing 12 with flexibility, so that the housing 12 may be sufficiently flexible to reach unhealthy and necrotic tissue in difficult-to-reach locations in a disc space. Additional flexibility can be achieved by manufacturing the housing 12 out of flexible synthetic materials. Suitable flexible synthetic materials are well-known in the art.

In accordance with one embodiment of the invention, and as depicted in FIG. 6, a complete second layer 74 of resistive heating elements 38 can be provided encircling, with respect to the mid-longitudinal axis, the first layer 36 of resistive heating elements 38 in its entirety. As depicted in FIG. 6, the complete second layer 74 of resistive heating elements 38 also extends in the proximal direction from the first position 40 to the second position 42. In accordance with the invention, the resistive heating elements 38 in the complete second layer 74 also are bipolar conductive coils. It is within the scope of this embodiment of the invention for the first layer 36 of resistive heating elements 38, and the complete second layer 74 of resistive heating elements 38 to be connected either in series or in parallel.

In accordance with one embodiment of the invention, and as embodied in FIG. 7, a partial distal second layer 76 of resistive heating elements 38 can be provided, encircling with respect to the mid-longitudinal axis a portion of the housing 12, disposed above a distal portion of the first layer 36 of resistive heating elements 38. As depicted in FIG. 7, the partial distal second layer 76 of resistive heating elements 38 is positioned proximate the distal end 20, and extends in the proximal direction, over a portion of the first layer 36, from the first position 40 to a third position 78 intermediate the first position 40 and the second position 42. In accordance with the invention, the resistive heating elements 38 in the partial distal second layer 76 also are bipolar conductive coils. It is within the scope of this embodiment of the invention for the partial distal second layer 76 of resistive heating elements 38, and the first layer 36 of resistive heating elements 38 to be connected either in series or in parallel.

In accordance with one embodiment of the invention, and as depicted in FIG. 8, a partial proximal second layer 80 of resistive heating elements 38 can be positioned encircling, with respect to the mid-longitudinal axis, a proximal portion of the first layer 36 of resistive heating elements 38, proximate the proximal end 18 and extending in the distal direction from the second position 42 to the third position 78. In accordance with the invention, the resistive heating elements 38 in the partial proximal second layer 80 also are bipolar conductive coils. It is within the scope of this embodiment of the invention for the partial proximal second layer 80 of resistive heating elements 38 and the first layer 36 of resistive heating elements 38 to be connected either in series or in parallel.

In accordance with the invention, and as depicted in FIGS. 1-8, the housing 12 includes a shield portion 82, projecting from the outer surface 14. The one or more complete or partial layers of resistive heating elements 38 are enclosed within the shield portion 82.

In accordance with the invention, a sensor 84 is provided on the outer surface 14, configured to measure impedance of spinal tissue proximate the sensor. As depicted in FIGS. 1-8, only one sensor 84 is shown, but it is within the scope of the invention for the ablation apparatus 10 to include a plurality of impedance measuring sensors 84. One of ordinary skill will recognize that when the ablation apparatus 10 is in air, the air acts as an open circuit, and impedance between the anode 24 and the cathode 34 is infinite. As depicted in FIG. 2, an electric wire 85 provides power to the sensor 84. Once the ablation apparatus is inserted into human tissue, e.g., a disc space between upper and lower vertebral bodies, the spinal tissue defines a finite impedance to a flow of anions and cations through the human tissue between the anode 24 and the cathode 34. This impedance is measured by the sensor 84. One of ordinary skill will further recognize that the impedance of healthy vertebral bone tissue is approximately 400Ω-500Ω, whereas the impedance of nerve tissue is approximately 50Ω-200Ω, and the impedance of unhealthy bone tissue in a tumor cell is approximately 50Ω-200Ω.

In accordance with another embodiment, the flow of ions through the spinal tissue is initially stimulated in the disc space via an Impedance Detection ("IMP")/Nerve Stimulation ("STM") switch 87. As depicted in FIG. 9, when the ablation apparatus 10 is inserted into the surgical site in the disc space, the switch 87 is in the IMP mode. Once the ablation apparatus 10 is in place in the surgical site, and its location is confirmed, the switch 87 changes to the STM mode, emitting a low power pulse to the sensor 84, stimulating the nerves to commence the ionic flow, enabling the sensor 84 to detect the spinal tissue impedance. Upon receipt of the lower power pulse, the patient's nerves will twitch, providing the surgeon with a visual indication that the ionic flow has commenced.

In accordance with another embodiment, the IMP/STM switch is used to stimulate the nerves, and to detect the nerve responses both before and after the treatment.

In accordance with the invention, the spinal tissue ablation apparatus described above can be included as part of a system for ablating unhealthy and necrotic tissue. In accordance with the invention, the system further includes a power generator 88. The power generator 88 includes a detector 90, a control module 92, a touch screen display 94, and a human interface panel 96. It is within the scope of the invention for the power generator 88 to be connected to the spinal tissue ablation apparatus 10 via electrically-conductive wires or via an RF link 98. It is preferred that, during surgery, the patient, the surgeon, and the ablation apparatus 10 are within a clean area, while the power generator 88 is located outside the clean area. Nevertheless, the touch screen display 94 is visible to the surgeon.

Detector 90 is configured to receive the respective spinal tissue temperatures measured by each of the first thermocouple 26, the second thermocouple 50, and the third thermocouple 56, and to receive the spinal tissue impedance measured by the sensor 84.

The detector 90 is further configured to integrate the respective spinal tissue temperatures with the spinal tissue impedance, and to route the integrated respective spinal tissue temperatures and the spinal tissue impedance, to the touch screen display 94. The spinal tissue impedance, and the respective spinal tissue temperatures, displayed on the touch screen display 94, are available to the surgeon during the surgery, providing the surgeon with feedback related to the status of the ablation procedure. Based on this feedback, the surgeon can, in his professional judgment, exercise control over the ablation apparatus 10. The control which the surgeon can exercise over the ablation apparatus 10 may include, not by way of limitation, one or more of: utilizing the human interface panel 96 to increase ablation heat by increasing electric current flow to the resistive heating elements 38; to increase ablation heat by reducing an amount of cooling water flowing through the housing, or reducing the flow rate of the cooling water; to decrease ablation heat by reducing electric current flow to the resistive heating elements 38; or to reduce ablation heat by increasing an amount of the cooling water flowing through the cooling system 60, or increasing the flow-rate of the cooling water. The surgeon also can utilize the flexibility of the housing 12 to adjust the location of the ablation apparatus 10 in the disc space, or to withdraw the ablation apparatus 10 from the disc space.

In accordance with the invention, a method is provided for ablating unhealthy spinal tissue in a surgical site in a patient. The method of the invention preferably uses both the spinal tissue ablation apparatus 10, and the power generator 88, as described above.

The method includes preparing a surgical site in the patient, e.g., a disc space between adjacent upper and lower vertebral bodies. The surgical site may include unhealthy spinal tissue, including unhealthy spinal nerve tissue, and also may include healthy spinal tissue. One of ordinary skill will recognize that a disc space also includes areas of projecting bone, particularly adjacent the posterior rim.

In accordance with the invention, the spinal tissue ablation apparatus 10 is inserted into the disc space. The flexible housing 12 is flexed, as necessary, to insert the ablation apparatus 10 fully to a desired location in the surgical site.

In accordance with the invention, the on/off switch 37, in the handle 39 is switched on, supplying electric current to at least the first layer 36 of the heating elements 38. The electric current provided to the at least the first layer 36 of the resistive heating elements 38 creates heat. In other embodiments, additional heat is applied by applying electric current to the at least the second layer 74 of resistive heating elements 38. In other embodiments, additional heat is applied by applying electric current to the at least the partial second distal layer 76 of resistive heating elements 38, or the partial second proximal layer 80 of resistive heating elements 38.

In accordance with the invention, temperature of spinal tissue proximate the anode 24 is measured by the first thermocouple 26.

In accordance with the invention, temperature of spinal tissue proximate the integrated position 52 is measured by the second thermocouple 50.

In accordance with the invention, temperature of spinal tissue proximate the proximal end 18, including spinal tissue proximate the patient's spinal cord, is measured by the third thermocouple 56.

In accordance with the invention, the IMP/STM switch 87 is switched to the STM position, to stimulate the nerves and detect the nerve responses before and after the treatment.

In accordance with the invention, the sensor 84 measures impedance of tissue proximate the ablation apparatus 10.

In accordance with the invention, the first thermocouple 26, the second thermocouple 50, and the third thermocouple 56 transmit their respective measured spinal tissue temperatures to the detector 90. The sensor 84 transmits its measured spinal tissue impedance to the detector 90. The detector 90 receives the measured spinal tissue temperatures and the measured spinal tissue impedance.

The detector 90 routes the spinal tissue impedance, and the spinal tissue temperatures, to the touch screen display 94. The touch screen display 94 is positioned to display all of the above data to the surgeon during the ablation procedure, and also is configured to display all of the data in any format required by the surgeon.

Based on the displayed spinal tissue impedance and spinal tissue temperatures, the surgeon can, in his professional judgment, exercise precise control over the ablation apparatus 10. In particular, the spinal tissue impedance informs the surgeon if he is ablating healthy tissue, or tumorous tissue, and whether the tissue being ablated is nerve tissue or bone tissue. In one embodiment, the surgeon can exercise control by using the human interface panel 96 which communicates via the control module 92 and RF link 98 to send control signals to the ablation apparatus 10.

Control available to the surgeon at the interface panel 96 includes, but is not limited to, increasing ablation heat by increasing electric current flow to the resistive heating elements 38; increasing ablation hear by reducing coolant water flow or flow rate; decreasing ablation heat by decreasing electric current flow to the resistive heating elements 38; decreasing ablation heat by increasing coolant water flow or flow rate. The surgeon further may utilize the flexibility of the housing 12, as needed, to adjust the position of the ablation apparatus 10 in the surgical site, including moving the ablation apparatus 10 away from the patient's spinal cord, or to withdraw the ablation apparatus 10 from the surgical site.

The flexible design of the housing enables the ablation apparatus 10 to accommodate different shapes and regions in the surgical site where unhealthy spinal nerve tissue may be present, to move the ablation apparatus 10 around projecting bones, e.g., at the posterior rim, and to move the ablation apparatus 10 away from healthy spinal tissue. The impedance-measuring sensor 84 measures spinal tissue impedance, the measured spinal tissue impedance corresponding to the physical state of the tissue at the surgical site during the ablation process. The thermocouples measure spinal tissue temperatures proximate the thermocouples during the ablation process. In particular, the third thermocouple, mounted in the housing proximate the proximal end monitors the temperature of spinal tissue proximate the patient's spinal cord. The closed loop resistive coil heating system with the thermocouple temperature feedback, the sensor impedance feedback, the human control interface panel, and the flexibility of the housing, all combine to provide the surgeon with precise control of power level and heat of the ablation apparatus, resulting in a faster ramp-up time, a shorter treatment time, more certain identification of the location of unhealthy spinal tissue, and avoidance of inadvertent ablation of healthy spinal tissue.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. For example, but not by way of limitation, the ablation apparatus 10 could include additional complete or partial layers of resistive heating elements, additional thermocouples, and additional sensors. Arrangement and display of spinal tissue data can be altered as desired to meet each surgeon's particular preference. If the material used to construct housing 12 is sufficiently flexible to meet a surgeon's needs, the air-filled gap 72 can be eliminated. In addition, the touch screen display 94 and the human interface panel 96 can be combined into a single screen or panel.

We claim:

1. A spinal tissue ablation apparatus comprising:
   an elongated housing, the housing including an outer surface, an inner surface, an interior space defined by the inner surface, a proximal end and a distal end, the proximal end and the distal end defining therebetween a mid-longitudinal axis;
   an anode defined on the outer surface at the distal end of the housing, the anode including an outer surface and an inner surface;
   at least one thermocouple disposed on the outer surface of the housing, the at least one thermocouple being configured to measure a temperature of spinal tissue proximate the at least one thermocouple;
   a cathode defined on the outer surface of the housing, intermediate the distal end and the proximal end;
   a cooling system disposed at least partially within the interior space;
   at least a first layer of resistive heating elements substantially encircling at least a portion of the outer surface of the housing relative to the mid-longitudinal axis, the at least the first layer of the resistive heating elements extending in a proximal direction from a first position proximate the cathode to a second position intermediate the first position and the proximal end of the housing;
   at least a second layer of resistive heating elements, the at least the second layer of resistive heating elements substantially encircling, relative to the mid-longitudinal axis, at least one of a portion of the at least the first layer of resistive heating elements extending from between the first position to the second position intermediate the first position and the proximal end, a portion of the at least the first layer of resistive heating elements extending from the first position to a third position intermediate the first position and the second position, a portion of the at least the first layer of resistive heating elements extending from the second position to a fourth position intermediate the first position and the second position; and
   at least one sensor mounted on the outer surface of the housing, the at least one sensor configured to measure tissue impedance proximate the at least one sensor.

2. An apparatus as recited in claim 1, wherein the at least one thermocouple includes a first thermocouple, the first thermocouple being disposed on the housing proximate the distal end.

3. An apparatus as recited in claim 2, wherein the at least one thermocouple includes a second thermocouple, the second thermocouple being disposed in an integrated position within the at least the first layer of resistive heating elements.

4. An apparatus as recited in claim 3, wherein the at least one thermocouple includes a third thermocouple, the third thermocouple being disposed on the housing proximate the proximal end.

5. An apparatus as recited in claim 4, wherein the apparatus is configured, during insertion of the apparatus into a patient's disc space, between two vertebral bodies, to position the third thermocouple proximate the patient's spinal cord.

6. An apparatus as recited in claim 1, wherein the at least one sensor is mounted on the distal end of the housing proximate the cathode and the anode.

7. An apparatus as recited in claim 1, wherein the cooling system includes a recirculating water system.

8. An apparatus as recited in claim 1, further comprising at least one elongated layer positioned between the inner surface and the interior space.

9. An apparatus as recited in claim 8, further comprising an elongated air-filled gap defined between the at least one layer and the inner surface, the air-filled gap being configured to provide flexibility to the housing.

10. An apparatus as recited in claim 1, further comprising a shield portion defined on the outer surface of the housing, the shield portion extending in the proximal direction from the first position, the shield portion being configured to enclose the at least the first layer and the at least the second layer of the resistive heating elements.

11. An apparatus as recited in claim 1, wherein the housing includes a flexible material.

12. A system for ablating unhealthy spinal tissue at a surgical site in a patient comprising:
    a spinal tissue ablation apparatus, the apparatus comprising:
      an elongated housing, the housing including an outer surface, an inner surface, an interior space defined by the inner surface, a proximal end and a distal end, the proximal end and the distal end defining therebetween a mid-longitudinal axis, a proximal direction and a distal direction;
      an anode defined on the outer surface at the distal end of the housing, the anode including an outer surface and an inner surface;
      at least one thermocouple disposed on the outer surface of the housing, the at least one thermocouple being configured to measure a temperature of spinal tissue proximate the at least one thermocouple;
      a cathode defined on the outer surface of the housing, intermediate the distal end and the proximal end;
      a cooling system disposed at least partially within the interior space;
      at least a first layer of resistive heating elements substantially encircling at least a portion of the outer surface of the housing relative to the mid-longitudinal axis, the at least the first layer of the resistive heating elements extending in a proximal direction from a first position proximate the cathode to a second position intermediate the first position and the proximal end of the housing;

at least a second layer of resistive heating elements, the at least the second layer of resistive heating elements substantially encircling, relative to the mid-longitudinal axis, at least one of a portion of the at least the first layer of resistive heating elements extending from between the first position to the second position intermediate the first position and the proximal end, a portion of the at least the first layer of resistive heating elements extending from the first position to a third position intermediate the first position and the second position, a portion of the at least the first layer of resistive heating elements extending from the second position to a fourth position intermediate the first position and the second position; and at least one sensor mounted on the outer surface of the housing, the at least one sensor configured to measure tissue impedance proximate the at least one sensor; and a power generator, the power generator including at least a detector, the detector being configured to receive the spinal tissue impedance measured by the at least one sensor, and the spinal tissue temperature measured by the at least one thermocouple, a control module, a touch screen display, the touch screen display being configured to display the spinal tissue impedance data, and the spinal tissue temperature, and a human interface panel, the human interface panel configured to control at least one of electric current to the at least the first layer of resistive heating elements and coolant flow to the cooling system.

13. A system as recited in claim 12, wherein the cooling system includes a recirculating water system.

14. A system as recited in claim 12, further comprising at least one elongated layer positioned between the inner surface and the interior space.

15. A system as recited in claim 14, further comprising an elongated air-filled gap defined between the at least one elongated layer and the inner surface, the air-filled gap being configured to provide flexibility to the housing.

16. A system as recited in claim 12, wherein the at least one thermocouple includes a first thermocouple, the first thermocouple being disposed on the housing proximate the distal end.

17. A system as recited in claim 16, wherein the at least one thermocouple further includes a second thermocouple, the second thermocouple being disposed in an integrated position within the at least a first layer of resistive heating elements.

18. A system as recited in claim 17, wherein the at least one thermocouple further includes a third thermocouple, the third thermocouple being disposed on the housing proximate the proximal end.

19. A system as recited in claim 12, further comprising a shield portion defined on the outer surface of the housing, the shield portion extending in the proximal direction from the first position proximate the cathode to the second position intermediate the first position and the distal end, the shield portion being configured to enclose the at least the first layer and the at least the second layer of the resistive heating elements.

20. A system as recited in claim 12, wherein the housing includes a flexible material.

21. A spinal tissue ablation apparatus comprising:

an elongated housing, the housing including an outer surface, an inner surface, an interior space defined by the inner surface, a proximal end and a distal end, the proximal end and the distal end defining therebetween a mid-longitudinal axis;

an anode provided on the outer surface at and/or adjacent the distal end of the housing;

at least one thermocouple provided on the outer surface of the housing for measuring a temperature of spinal tissue proximate the at least one thermocouple;

a cathode provided on the outer surface of the housing intermediate the distal end and the proximal end;

a cooling system disposed at least partially within the interior space;

a first layer of resistive heating elements substantially encircling at least a portion of the outer surface of the housing relative to the mid-longitudinal axis, the first layer of the resistive heating elements extending between a first position proximate the cathode to a second position intermediate the first position and the proximal end of the housing;

a second layer of resistive heating elements, the second layer of resistive heating elements substantially encircling, relative to the mid-longitudinal axis, at least one of a portion of the first layer of resistive heating elements extending from between the first position to the second position intermediate the first position and the proximal end, a portion of the first layer of resistive heating elements extending from the first position to a third position intermediate the first position and the second position, a portion of the first layer of resistive heating elements extending from the second position to a fourth position intermediate the first position and the second position; and at least one sensor provided on the outer surface of the housing for measuring tissue impedance proximate the at least one sensor.

22. An apparatus as recited in claim 21, wherein the at least one thermocouple includes a first thermocouple, the first thermocouple being provided on the housing proximate the distal end.

23. An apparatus as recited in claim 22, wherein the at least one thermocouple includes a second thermocouple, the second thermocouple being disposed in an integrated position within the at least the first layer of resistive heating elements.

24. An apparatus as recited in claim 23, wherein the at least one thermocouple includes a third thermocouple, the third thermocouple being provided on the housing proximate the proximal end.

25. An apparatus as recited in claim 24, wherein the apparatus is configured, during insertion of the apparatus into a patient's disc space, between two vertebral bodies, to position the third thermocouple proximate the patient's spinal cord.

26. An apparatus as recited in claim 21, wherein the at least one sensor is provided on the distal end of the housing proximate the cathode and the anode.

27. An apparatus as recited in claim 21, wherein the cooling system includes a recirculating water system.

28. An apparatus as recited in claim 21, further comprising at least one elongated layer positioned between the inner surface and the interior space.

29. An apparatus as recited in claim 28, further comprising an elongated air-filled gap defined between the at least one layer and the inner surface.

30. An apparatus as recited in claim 21, further comprising a shield portion defined on the outer surface of the housing, the shield portion extending in the proximal direction from the first position, the shield portion being configured to enclose the first layer and the second layer of the resistive heating elements.

31. An apparatus as recited in claim 21, wherein the housing includes a flexible material.

* * * * *